United States Patent [19]

Handke

[11] Patent Number: 4,913,401

[45] Date of Patent: Apr. 3, 1990

[54] VALVE APPARATUS

[75] Inventor: Patrick M. Handke, Monroeville, Pa.

[73] Assignee: Respironics, Inc., Monroeville, Pa.

[21] Appl. No.: 302,187

[22] Filed: Jan. 26, 1989

[51] Int. Cl.[4] .............................................. F16K 7/02
[52] U.S. Cl. ..................................... 251/342; 251/900
[58] Field of Search ................................. 251/342, 900

[56] References Cited

U.S. PATENT DOCUMENTS

| | | |
|---|---|---|
| 274,447 | 3/1883 | Kennish . |
| 1,418,592 | 6/1922 | McGee . |
| 2,666,432 | 1/1954 | Stanton . |
| 2,706,101 | 4/1955 | Cantor ........................... 251/342 X |
| 3,450,146 | 6/1969 | Edwards . |
| 3,977,409 | 9/1976 | Brendling . |
| 4,106,675 | 8/1978 | Taylor ............................. 251/342 X |
| 4,142,645 | 3/1979 | Walton ............................ 251/342 X |
| 4,181,140 | 1/1980 | Bayham et al. . |
| 4,267,834 | 5/1981 | Barger ............................. 251/342 X |
| 4,294,247 | 10/1981 | Carter et al. . |
| 4,300,571 | 11/1981 | Waldbillig . |

Primary Examiner—Robert G. Nilson
Attorney, Agent, or Firm—Carothers & Carothers

[57] ABSTRACT

A valve apparatus for installation in a fluid conveying conduit which is operable by deformation of valve elements to open and permit fluid flow therethrough.

11 Claims, 1 Drawing Sheet

VALVE APPARATUS

BACKGROUND OF THE INVENTION

In the valve arts there are well known a variety of valve structures which are disposed within elongated tubular members for the purpose of controlling fluid flow within such tubular members. Among such valves are a variety of valve structures which remain normally in one state, either open or closed, and which are changed to the opposite state by manually induced deformation or movement of valve elements within the tube structure. Some such valves have taken the form of valve assemblies which are inserted within a fluid carrying conduit while others have been formed in unitary fashion with the fluid carrying conduit.

Among the prior art which is representative of such valves in U.S. Pat. No. 4,267,834 which discloses a deformable squeeze valve element having a rigid tube running through it, the squeeze valve being operable by squeezing of projections thereon from an undeformed state to a deformed state whereby a fluid flow passage is opened. U.S. Pat. No. 3,977,409 discloses a valve structure within a fluid carrying tube which is opened by moving a pair of adjacent valve elements to an offset orientation with respect to one another by deforming the flexible tube in which they are disposed. U.S. Pat. No. 4,106,675 discloses a squeeze valve comprised of a rigid ball member disposed within a flexible resilient tube.

U.S. Pat. No. 1,418,592 discloses a syringe valve which is operable upon deformation of a flexible tube within which it is disposed by lateral bending of the tube. A valve with similar operating action is disclosed by U.S. Pat. No. 3,450,146. U.S. Pat. No. 274,447 discloses another squeeze valve consisting of resiliently flexible elements formed integrally with a tube structure.

BRIEF SUMMARY OF THE INVENTION

The present invention contemplates a novel and improved squeeze valve assembly for installation preferably within a terminal end portion of a resiliently flexible fluid conveying conduit, and a valve including such a fluid conveying conduit wherein sealed closure of the valve is maintained by continuous peripheral contact between a resiliently flexible ring seal and the inner periphery of the fluid conveying conduit, and a further peripheral seal between the inner periphery of the ring and an external peripheral portion of an elongated assembly of valve elements. A structure is provided to support the ring seal with respect to the valve element assembly and within the fluid conveying conduit such that the continuous peripheral seal is maintained in the normal state and is broken only upon squeezing of the ring by application of pressure, such as manual finger pressure, applied diametrically to the exterior of the fluid conveying tube at the location of the ring seal therein.

The invention affords improved reliability of performance and ease of operation, improved sealing characteristics, enhanced ease of valve assembly and installation, improved economy of manufacture, and related advantages.

It is accordingly one object of the invention to provide a novel and improved squeeze valve element having resiliently flexible members which are deformable to change the valve from an open state to a closed state.

A more specific object of the invention is to provide a squeeze valve assembly wherein a generally elongated, stepped cylindrical valve structure includes a ring seal encompassing the same with the valve structure and ring assembly being insertable within a fluid conveying conduit to provide valved control of fluid flow within the conduit.

These and other objects and further advantages of the invention will be more readily appreciated upon consideration of the following detailed description and the accompanying drawings, in which.

Figure 1:
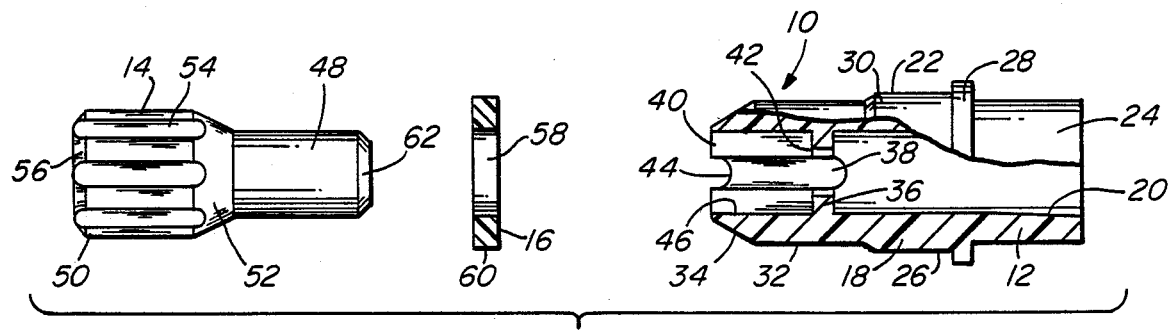
FIG. 1 is an axially exploded, partially sectioned side elevation of the valve assembly according to this invention showing the individual elements of the valve assembly.

There is generally indicated at 10 in FIGS. 1 and 2, a valve assembly according to one presently preferred embodiment of the instant invention and comprised of a generally stepped cylindrical valve inlet member 12, a generally stepped cylindrical valve outlet member 14, and a ring seal alternatively referred to hereinafter as an O-ring seal 16. An O-ring commonly has a generally circular cross section while the cross section of the ring seal shown in the figures is generally rectangular. For purposes of this description, both are intended to be included within the meaning of the term "O-ring" and equivalent terms used herein. References herein to inlet and outlet ends, members, and so forth are included for purposes of convenience and clarity. In fact, the disclosed valve is operable to support fluid flow in either of the opposed flow directions.

Inlet member 12 comprises an elongated generally stepped cylindrical body member 18 having an axial through bore 20 and a stepped cylindrical exterior periphery 22 which includes an adapter end portion 24 extending from one axial end thereof, a tube receiving portion 26 extending coaxially from the opposed axial end thereof, and an enlarged diameter stop portion 28 disposed coaxially intermediate and adjacent to the portions 24 and 26. Tube receiving portion 26 includes a larger diameter seal portion 30 and a relatively smaller diameter axial extension 32 which includes adjacent its axially outermost end a truncated conical end portion 34.

Intermediate the axial ends of through bore 20 there is formed a radially inwardly projecting generally annular stop portion 36 against which outlet number 14 is seated in assembly of the valve 10 as will be described hereinbelow. At least one, and preferably a pair of diametrically opposed undercuts 38 extend axially within bore 20 from the inner open end 40 thereof to a point preferably beyond the abutment surface 42 of stop portion 36. Where the undercut 38 intersects conical surface 34, an axially extending recess for opening 44 is formed which operates as part of a fluid flow passage in passing fluid through the valve structure, as will be described hereinbelow.

Figure 2:
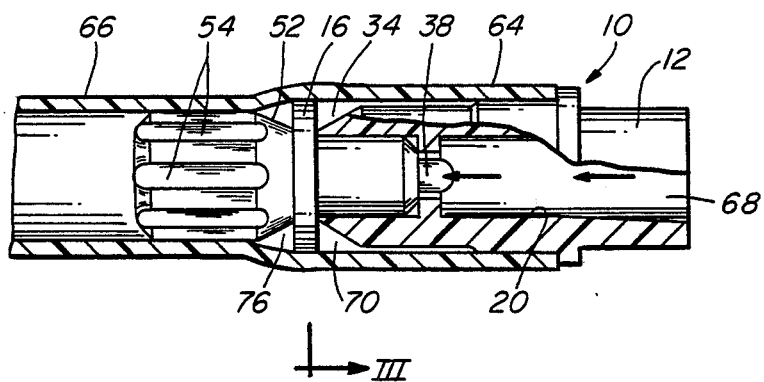
FIG. 2 is a side elevational view showing the valve elements assembled and installed within a terminal end portion of a fluid conveying conduit.
Figure 3:
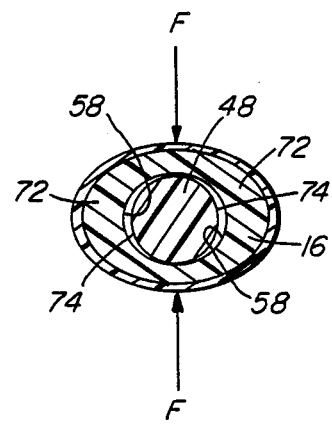
FIG. 3 is a transverse section taken on line III—III of FIG. 2 and showing actuation of the valve.

That portion of bore 20 extending axially intermediate stop portion 36 and open end 40, and designated in FIG. 1 as 46 is of a size to snugly receive a generally cylindrical extension portion 48 of outlet member 14.

The opposed axial end portion of member 14 is comprised of an enlarged diameter barrel portion 50 disposed coaxially with respect to portion 48 and joined therewith by an intervening conical portion 52. A plurality of axially extending grooves 54 are distributed circumferentially about the periphery of barrel portion 50, the axial ends of the grooves 54 intersecting conical surface 52 and an axially opposed conical end portion 56 of barrel portion 50 to provide a further portion of a fluid flow passage for directing fluid flow through the valve 10 in a manner to be described hereinbelow.

O-ring seal 16 is provided with an inner periphery 58 of a diameter to provide sealing engagement with a portion of extension 48 axially adjacent to conical portion 52 of outlet number 14. The O-ring seal 16 also is provided with an outer periphery 60 of a diameter to seal the inner periphery of a resiliently flexible tube member in which the valve assembly is received.

Inlet member 12 and outlet member 14 may be formed as by molding thereof from plastic or hard elastomer such as polycarbonate or polyvinyl chloride for example. O-ring 16 may be formed from any suitable elastomer such as natural rubber for example, having the requisite properties of flexibility to conform to engaged surfaces to seal thereon, and having the requisite flexibility to permit manual deformation of the O-ring in the assembled valve for opening the valve. In the assembled configuration, as shown in FIG. 2, O-ring 16 is placed coaxially onto extension portion 48 of outlet member 14 adjacent to conical surface 52 thereof and extension portion 48 is received within bore portion 46 of inlet valve member 12 with the end face 62 of extension portion 48 in abutting engagement with abutment surface 42 of stop portion 36.

Preferably, the assembly of components as described is secured by the application of suitable adhesive to the mating surfaces of bore portion 46 and extension portion 48 provided however that the adhesive does not block or otherwise interfere in any way with the fluid passage provided by undercuts 38. The assembled valve structure thus is as shown in FIG. 2 and as assembled is received within preferably the terminal end portion 64 of a resiliently flexible fluid conveying tube member 66 to control by the valving action the flow of fluid therewithin. For example, and as shown in FIG. 2, fluids such as air entering valve 10 via the open end 68 of bore 20 passes within bore 20 to undercuts 38 and thence via the undercuts 38 along the exterior periphery of extension portion 48 to recesses 44 which are open to a space 70 defined within tube 66 on the upstream side of O-ring.

Upon applying manual pressure by finger squeezing or the like to tube 66 at the axial location of O-ring 16, the O-ring 16 is deformed by flattening thereof against extension portion 48. As a result, the opposed side portions 72 of O-ring 16 which are offset generally by 90 degrees from the location of squeezing force F, tend to bulge radially outward thereby opening respective passages 74 between the inner periphery 58 of O-ring 16 and the adjacent periphery of extension portion 48. Air within space 70 thus is given free access to a space 76 formed adjacent the opposed side of O-ring 16, whereby the air thence may flow via grooves 54 to the end of valve 10 and further within tube 66. Upon release of the manual squeezing force F, O-ring 16 resiles to its undeformed state thus again sealing continuously with the inner periphery of tube 66 and the outer periphery of extension portion 48 and thus closing the valve 10.

It will be noted that in the assembled valve, O-ring 16 is confined axially between the conical surface portions 34 and 52, whereby pressure applied in either of spaces 70 or 76 and acting on the respective confronting surface of O-ring 16 will not move the O-ring 16 axially.

It will be appreciated that adapter 12 may be suitably formed to connect with any suitable supply of fluid flow such as a syringe which may be used as a pump to pump air or other fluid via bore 20 and undercuts 38 through the valve 10 and onward within conduit 66. Alternatively, adapter end portion 12 may be received within an open end portion of a flexible tube similar in all salient respects to end portion 64 of tube or conduit 66, for connection thereby to any suitable source of fluid flow.

From the above description, it will be appreciated that I have invented a new and improved valve assembly for installation within a flexible fluid flow conduit to control flow within the conduit in response to application of manual force directed generally radially with respect to the axial extent of the tube. The invention also contemplates the combination of the described valve element or assembly and a fluid conveying conduit in which the valve assembly is installed.

Of course, I have envisioned various alternative and modified embodiments apart from the above disclosed presently preferred embodiment of the invention. Accordingly, the invention is to be construed broadly and limited only by the scope of the claims appended hereinto. For example, in an alternative embodiment a sleeve encompasses the valve members as part of an overall valve structure with the valve and sleeve assembly being adapted for installation in a fluid conveying conduit.

I claim:

1. A valve apparatus adapted for installation within a fluid conveying conduit comprising:
   an elongated body means having a pair of axially spaced opposed ends and a flow passage means which extends therebetween and includes an external peripheral portion of said body means located axially intermediate said opposed ends;
   a resiliently deformable ring means encompassing said body means with and inner peripheral portion thereof in peripheral sealing engagement with said external peripheral portion of said body means to close said fluid flow passage means;
   said resiliently deformable ring means having an outer peripheral portion which is adapted to engage the interior periphery of such a fluid conveying conduit in continuous circumferentially extending sealing engagement therewith; and
   said resiliently deformable ring means being operable upon compressive deformation thereof in a direction generally radially inward with respect to the longitudinal axis of said body means to open said fluid flow passage means radially intermediate said inner peripheral portion thereof and said external peripheral portion of said body means to permit fluid flow through said valve within said fluid flow passage means.

2. The valve as set forth in claim 1 wherein said body means is a generally stepped cylindrical body.

3. The valve as set forth in claim 2 wherein said fluid flow passage means includes an elongated passage means extending longitudinally within said body means.

4. The valve as set forth in claim 3 wherein said body means includes a two piece body assembly comprised of an elongated inlet member having a bore means extending longitudinally from one end thereof and an elongated outlet member including an extension portion which is received within said bore.

5. The valve as set forth in claim 4 wherein said inlet member includes said elongated passage means.

6. The valve as set forth in claim 5 wherein said bore and said elongated passage means communicate with each other in fluid flow conveying relation.

7. The valve as set forth in claim 6 wherein said bore and said elongated passage means are formed by a generally stepped through bore extending axially within said inlet member.

8. The valve as set forth in claim 7 wherein said bore includes radially outward undercut portions extending longitudinally thereof which cooperate with said extension portion to define a part of said fluid flow passage means extending within said body means.

9. The valve as set forth in claim 8 wherein said external peripheral portion is located adjacent the external juncture between said inlet and outlet members.

10. The valve as set forth in claim 9 wherein said outlet member includes an enlarged diameter barrel portion adapted to engage the inner periphery of such a fluid conveying conduit and said barrel portion includes longitudinally extending groove means which form a portion of said fluid flow passage means.

11. The valve as set forth in claim 1 additionally including elongated resiliently deformable sleeve means encompassing said body means and maintained in continuous peripheral sealed engagement with said outer peripheral portion of said resiliently deformable ring means and with a portion of said body means located axially to one side only of said resiliently deformable ring means.

* * * * *